United States Patent [19]

Bark

[11] Patent Number: 5,171,269
[45] Date of Patent: Dec. 15, 1992

[54] MAMMARY PROSTHESIS

[75] Inventor: Jeffrey E. Bark, Paso Robles, Calif.

[73] Assignee: Medical Engineering Corporation, Racine, Wis.

[21] Appl. No.: 752,288

[22] Filed: Aug. 29, 1991

[51] Int. Cl.⁵ ............................................. A61F 2/12
[52] U.S. Cl. ............................................. 623/8; 623/7
[58] Field of Search ............................... 623/7, 8, 11

[56] References Cited

U.S. PATENT DOCUMENTS

| | | | |
|---|---|---|---|
| 2,842,775 | 7/1958 | Pangman | 3/36 |
| 3,301,260 | 1/1967 | Ray | 623/7 |
| 3,559,214 | 2/1971 | Pangman | 3/36 |
| 3,663,968 | 5/1972 | Mohl et al. | 3/36 |
| 3,683,424 | 8/1972 | Pangman | 623/8 |
| 3,986,213 | 10/1976 | Lynch | 623/8 |
| 4,205,401 | 6/1980 | Frisch | 3/36 |
| 4,731,081 | 3/1988 | Tiffany et al. | 632/8 |
| 4,944,750 | 7/1990 | Cox, Jr. | 623/8 |
| 4,955,907 | 9/1990 | Ledergerber | 623/8 |
| 4,960,425 | 10/1990 | Yan et al. | 623/8 |

*Primary Examiner*—David Isabella
*Assistant Examiner*—Gina Gualtieri
*Attorney, Agent, or Firm*—Quarles & Brady

[57] ABSTRACT

A mammary prosthesis for augmentation mammoplasty is comprised of a shell containing an insoluble, fibrous material which when the shell is inflated with inflating fluid adjusts the feel and appearance of the inflated shell to approximate natural mammary tissue. The shell is sealed except for a valve which can be used to inflate the shell.

5 Claims, 1 Drawing Sheet

MAMMARY PROSTHESIS

FIELD OF THE INVENTION

This invention relates generally to the field of medical implants and, more particularly, to mammary prostheses.

BACKGROUND OF THE INVENTION

Augmentation mammoplasty, that is, surgical augmentation of the breasts, is a common cosmetic surgical procedure that has been performed for many years. This procedure usually entails making a surgical incision to create a pocket in the breast and then inserting a mammary prosthesis, generally shaped similar to the human breast, into the pocket.

Mammary prostheses are well known in the art and generally take several forms. There are single unitary mammary prostheses which comprise a shell of physiologically inert material, such as silicone rubber or the like, which is filled with a silicone gel or a saline solution and then sealed. Inflatable mammary prostheses also are available and generally include a hollow shell of physiologically inert material, such as silicone rubber, which is implanted and then filled with a saline solution during surgery to achieve the appropriate prosthesis and breast size. In addition to the single shell inflatable mammary prosthesis, an inflatable bilumen or double shell mammary prosthesis is also available. The inflatable bilumen mammary prosthesis generally includes an inner shell filled with a gel which is positioned within an outer shell that can be filled with liquid through a valve to achieve the desired breast augmentation.

Both the single shell inflatable mammary prosthesis and the inflatable bilumen mammary prosthesis advantageously permit the size of the mammary prosthesis to be varied by altering the amount of liquid admitted to the prosthesis. However, the single shell prosthesis does possess several advantages. First, it can be folded or rolled into a very compact form and thus inserted through a relatively small incision. Second, it contains no gel which can migrate if the shell is ruptured. However, there are disadvantages to the current single shell prosthesis. The walls of the single shell prosthesis are more likely to adhere together or crease which can structurally weaken the shell. In addition, when completely filled with the preferred liquid, saline solution, the fluid hydraulic properties of a single shell prosthesis can result in an unnatural feel.

There is a need for a single shell inflatable mammary prosthesis which does not possess the disadvantages of the prior art prostheses.

BRIEF SUMMARY OF THE INVENTION

It is an object of the present invention to disclose an improved single shell mammary prosthesis.

The mammary prosthesis of the present invention comprises an inflatable shell which contains an insoluble, fibrous material which both prevents the walls of the shell from creasing or adhering together before the shell is filled with inflating liquid and adjusts the fluid hydraulic properties of the shell when it is inflated with liquid to more closely approximate those of natural mammary tissue.

The amount of the fibrous material which is contained in the shell should be sufficient to prevent the top of the shell from collapsing down and adhering to the base when the shell is uninflated and to adjust the feel and appearance of the inflated shell to closely approximate those of natural mammary tissue. The exact amount of the fibrous material in a shell will depend upon the density of the fibrous material and the internal volume of the shell.

In a preferred embodiment of the invention, an improved, single shell mammary prosthesis comprises a physiologically inert shell which has an internal volume of about 300 mls. It contains about 4 mg of a fibrous material, such as polyester, which has a density of about 0.01 mg/cc. If desired, the outer wall of the shell can be textured or covered with foam or fabric to reduce the possibility of encapsulation.

The features of the invention believed to be novel are set forth with particularity in the appended claims. However, the invention itself, both as to organization and method of operation, together with further objects and advantages thereof may best be understood by reference to the following description taken in conjunction with the accompanying drawings in which:

DESCRIPTION OF THE PREFERRED EMBODIMENT

Figure 1:
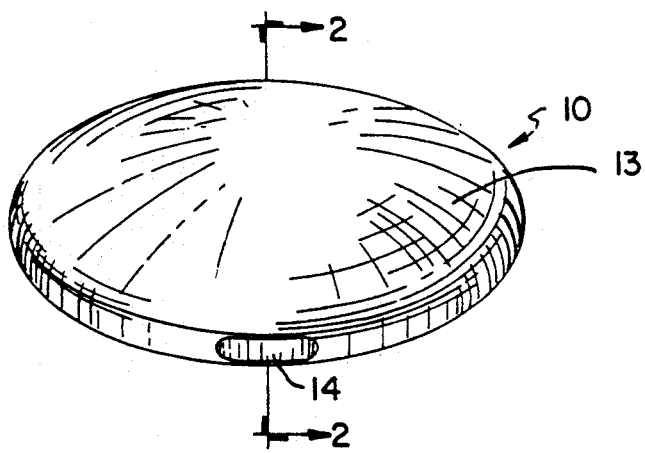
FIG. 1 is a perspective view of a preferred embodiment of a mammary prosthesis of the present invention in an uninflated state.
Figure 2:
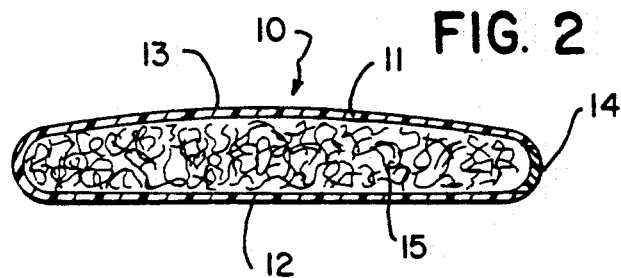
FIG. 2 is a view taken along lines 2—2 of FIG. 1.
Figure 3:
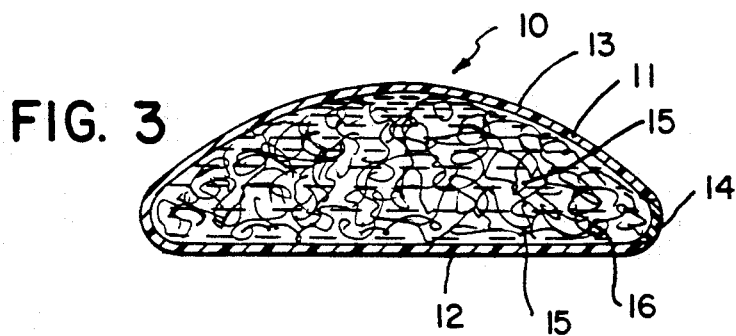
FIG. 3 is a view like that of FIG. 2 of the prosthesis of FIG. 1 in an inflated state.

Referring now to the drawings, an improved mammary prosthesis 10 is illustrated in perspective in FIG. 1 and is shown in a cross sectional elevational view in its uninflated and inflated states in FIGS. 2 and 3, respectively.

As seen in FIGS. 1 to 3, the prosthesis 10 is comprised of a shell 11 having a substantially flat base 12, a dome shaped top 13 and a self-sealing disc valve 14. Both the shell 11 and the disc valve 14 are manufactured from a physiologically inert (safe) material, such as silicone rubber or the like. The shell 11, which typically has relatively thin walls, may have either a teardrop shape or a round or a hemispherical shape depending on the desired mammary augmentation.

As seen best in FIGS. 2 and 3 the interior of the shell 11 contains solid strands of a fibrous material 15, as well as an inflating liquid 16, such as saline solution.

As seen in FIG. 2 the fibrous material 15 structurally supports the shell 11 in the uninflated state and prevents the top 13 from collapsing down upon and adhering to the base 12 or from creases forming in the shell wall. The fibrous material 15 helps to fill the inflated shell, as seen in FIG. 3, and to adjust the feel and appearance of the inflated shell to approximate that of natural mammary tissue.

Figure 4:
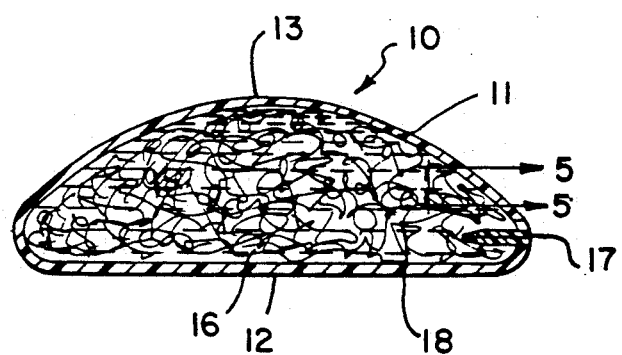
FIG. 4 is a view like that of FIG. 3 of another embodiment of a mammary prosthesis of the present invention.
Figure 5:
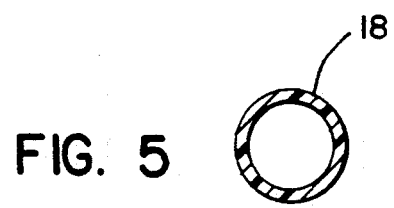
FIG. 5 is an enlarged sectional view of a strand of fibrous material taken along lines 5—5 in FIG. 4.

In FIGS. 4 and 5 another embodiment is shown in which a duckbill valve 17, seen only in FIG. 4, replaces the disc valve 14. The valve 17 is used to introduce inflating liquid into the interior hollow of the shell 11.

In the embodiment of FIGS. 4 and 5, the solid strands of fibrous material 15 of the first embodiment are replaced, in whole or in part, with hollow fibrous strands 18 seen only in FIG. 5.

The shell 11 is preferrably prepared by dipping a mold into the shell material. Once the shell is cured and removed from the mold the fibrous material 15 or 18 can be introduced into the shell through an opening in which a suitable valve is later sealed.

At time of surgery, the prosthesis 10 is rolled into a relatively compact form and inserted into a surgically created pocket. The shell 11 is then inflated by introducing an inflating liquid 16 through the disc valve 14 or the duckbill valve 17.

The preferred fibrous material comprises coiled solid strands 15 of polyester having a density of about 0.01 mg/cc and a diameter of about 0.001 inches. However, the fibrous material can be of any suitable material which is insoluble in the inflating liquid which is usually saline solution. The amount of the fibrous material placed in the shell should be an amount which results in the inflated prostheses approximating the feel and appearance of natural tissue.

The foregoing description has been for purposes of illustration. While only certain preferred features of the invention have been described, many modifications and changes will occur to those skilled in the art. For example, the terms "inflating fluid," "saline solution," "insoluble" and "fibrous" as used herein are intended to include materials which function in a similar manner. In addition, the present invention also can be used to improve the feel and appearance of bilumen prostheses by putting the fibrous material in the inflatable outer shell. Therefore, it is to be understood that the claims are intended to cover all such modifications and changes as fall within the true spirit of the invention.

I claim:

1. A mammary prosthesis comprising:
   (a) a hollow shell of physiologically inert material having a relatively flat base and a collapsible domed top;
   (b) an insoluble, fibrous material partially filling said shell and preventing the collapsible top and bottom from touching when the shell is uninflated, said fibrous material being present in an amount and having a density which when the shell is filled with an inflating liquid results in the inflated prosthesis having fluid hydraulic properties approximating natural mammary tissue;
   (c) an inflating liquid filling the remainder of and inflating said shell; and
   (d) valve means sealing said hollow shell and providing means by which inflating liquid can be introduced into or removed from said shell.

2. A prosthesis of claim 1 in which the fibrous material comprises coiled solid plastic strands.

3. A prosthesis of claim 1 in which the fibrous material comprises coiled hollow plastic strands.

4. A prosthesis of claim 1 in which an outer surface of the shell is textured.

5. An implantable mammary prosthesis comprising:
   (a) A hollow inflatable shell of physiologically inert material having a relatively flat base and a collapsible domed top;
   (b) an insoluble, fibrous polyester material partially filling said shell and preventing the top and bottom from touching when the shell is uninflated, said fibrous material having a density of about 0.01 mg/cc and being present in an amount which when the shell is filled with saline solution results in the inflated prosthesis having the feel and appearance of natural mammary tissue; and
   (c) saline solution filling the remainder of and inflating said shell; and
   (d) valve means sealing said hollow shell and providing means by which saline solution can be introduced into or removed from said shell.

* * * * *